US00PP27162P2

(12) United States Plant Patent
Kordes

(10) Patent No.: US PP27,162 P2
(45) Date of Patent: Sep. 20, 2016

(54) MINIATURE ROSE PLANT NAMED 'KORPOT050'

(50) Latin Name: *Rosa hybrida*
Varietal Denomination: KORpot050

(71) Applicant: Tim-Hermann Kordes, Klein Offenseth-Sparrieshoop (DE)

(72) Inventor: Tim-Hermann Kordes, Klein Offenseth-Sparrieshoop (DE)

(73) Assignee: W. Kordes' Söhne Rosenschulen GmbH & Co KG, Offenseth-Saprrieshoop (DE)

( * ) Notice: Subject to any disclaimer, the term of this patent is extended or adjusted under 35 U.S.C. 154(b) by 106 days.

(21) Appl. No.: 14/544,456

(22) Filed: Jan. 7, 2015

(51) Int. Cl.
*A01H 5/02* (2006.01)

(52) U.S. Cl.
USPC ..... Plt./119

(58) Field of Classification Search
USPC ..... Plt./116, 119, 122
See application file for complete search history.

*Primary Examiner* — Susan McCormick Ewoldt

(57) ABSTRACT

A new and distinct variety of rose with long lasting, novel orange-red flowers, and attractive foliage with very good disease resistance. It exhibits compact, upright to bushy growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORpot050'.

CROSS REFERENCES AND FEDERAL R&D STATEMENT

There are no cross referenced or related applications. This variety was developed without the aid of any research grant.

BACKGROUND OF THE INVENTION

The new variety of rose plant of the present invention originated from a controlled crossing in a breeding program of two distinct parents during the summer of 2011. The crossing was between an un-named seedling, the seed parent, and another un-named seedling, the pollen parent by the same inventor.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORpot050'.

SUMMARY OF THE INVENTION

The new rose plant may be distinguished from its seed parent, an un-named seedling, by the following combination of characteristics:

1. 'KORpot050' has orange-red flowers with high centers, whereas the un-named seedling has red flowers which are rounded in shape.
2. 'KORpot050' has very good shelf-life, whereas the un-named seedling has average shelf life.

The new rose plant may be distinguished from its pollen parent, an un-named seedling, by the following combination of characteristics:

1. 'KORpot050' has medium-sized orange-red flowers, whereas the un-named seedling has large red flowers.
2. 'KORpot050' has a compact growth habit, whereas the un-named seedling has an upright growth habit.

The objective of the hybridization was to create a new and distinct rose plant with unique qualities, such as:

1. Compact and uniform growth and flowering under greenhouse conditions when grown as a potted floral plant;
2. Abundant, long lasting, and attractive flowers and foliage;
3. Resistance to diseases encountered in greenhouse and nursery culture; and
4. Suitability for production from softwood cuttings in floral and nursery containers.

This combination of qualities is not present in prior rose cultivars known to the inventor. These objectives have been substantially achieved and in that distinguish 'KORpot050' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORpot050' was selected in April 2012 from the seedling beds to be asexually propagated for further evaluation. The first asexual propagation of 'KORpot050' was done by rooting softwood cuttings in June 2012 at the inventor's nursery in Offenseth-Sparrieshoop, Germany.

These initial and other subsequent propagations conducted in controlled environments demonstrate that 'KORpot050' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORpot050'.

DETAILED BOTANICAL DESCRIPTION

The following is a description of 'KORpot050', as observed growing in December, 2014 in a nursery in Jackson County, Oreg. on plants of 8 months of age. Color references are made using The Royal Horticultural Society (London, England) Colour Chart, 2001 except where common terms of color are used.

For a comparison, several physical characteristics of the rose variety 'KORpolare', a rose variety from the same inventor described and illustrated in U.S. Plant Pat. No. 18,840 and issued on May 27, 2008 are compared to 'KORpot050' in Chart 1.

CHART 1

| Characteristic | 'KORpot050' | 'KORpolare' |
|---|---|---|
| General tonality on open flower. | Red Group 43B. | Red Group 53A to 53B with intonations of Red-Purple Group 60A |
| Average petal count under normal conditions. | 30. | 55. |
| Average size of sepals. | 20 to 25 mm (l) × 6 to 7 mm (w). | 35-40 mm long × 9 mm wide. |

Parents:

*Seed parent*.—An un-named seedling.

*Pollen parent*.—An un-named seedling.

Classification:

*Botanical classification*.—*Rosa hybrida* 'KORpot050'.

*Commercial classification*.—Miniature rose.

FLOWER AND FLOWER BUD

Blooming habit: Recurrent.

Flower bud:

*Size*.—Upon opening, 30 mm in length from base of receptacle to distal end of bud and 15 mm diameter at its widest point.

*Bud form*.—Long. Pointed ovoid. High centered.

*Bud color*.—As sepals first unfold, bud color is Red Group 45C. When ¼ open, the upper surface of petals is Red Group 44B, and the lower surface is Red Group 45C.

*Sepals*.—Color: Upper surface Yellow-Green Group 146B. Lower surface Yellow-Green Group 146B. Size: Average 20 to 25 mm (l)×6 to 7 mm (w). Calyx diameter: 50 to 60 mm. Shape: Very weak foliaceous appendages on one of the five sepals. Apex: Typically apiculate, occasionally cirrose. Base: Flat at union with receptacle. Quantity: Five. Surface texture: Upper side: Hoary. Lower surface: Hispid. Margins: Cilliate. Stipitate glands: Abundant on lower surface only.

Flower bloom:

*Fragrance*.—Moderate.

*Duration*.—On the plant 15 to 18 days. Senesced petals drop away cleanly.

*Size*.—Medium-sized for a miniature rose. When open, the average flower diameter is 50 to 55 mm and the average flower height is 25 to 35 mm.

*Form*.—Shape: Round. Shape of flower when viewed from the side: Upon opening, upper part: Flat. Upon opening, lower part: Flattened convex. Open flower, upper part: Flat. Open flower, lower part: Flattened convex.

Color:

*Upon opening, petals*.—Outermost petals: Outer Side: Red Group 45C. Inner Side: Red Group 44B. Innermost petals: Outer Side: Red Group 50A, with intonations of White Group 155A on the basal zone. Inner Side: Red Group 43B, with intonations of White Group 155A on the basal zone.

*Upon opening, basal petal spots*.—Basal petal spot, outermost petals: Outer Side: Red-Purple Group 63B. Inner Side: White Group 155A. Size: Average 4 to 5 mm (h)×5 to 6 mm (w). Basal petal spot, innermost petals: Outer Side: White Group 155A. Inner Side: White Group 155A. Size: Average 1 mm (h)×2 mm (w).

*After opening, petals*.—Outermost petals: Outer Side: Red Group 45C, with intonations of White Group 155A occasionally present on basal zone. Inner Side: Red Group 44B, with intonations of White Group 155A occasionally present on midrib. Innermost petals: Outer Side: Red Group 50A, with intonations of White Group 155A present on midrib. Inner Side: Red Group 44C, with intonations of White Group 155A present on midrib.

*After opening, basal petal spots*.—Basal petal spot, outermost petals: Outer Side: White Group 155A. Inner Side: White Group 155A. Size: Average 1 to 5 mm (h)×2 to 8 mm (w). Basal petal spot, innermost petals: Outer Side: White Group 155A. Inner Side: White Group 155A. Size: Average 1 to 5 mm (h)×2 to 5 mm (w).

General tonality: On open flower Red Group 43B. No change in the general tonality at the end of the 8th day. Afterwards, general tonality is Red Group 43D.

Petals:

*Petal count*.—Double. Approximately 30 petals under normal conditions.

*Petal reflex*.—Outermost petals reflex slightly. Reflex occurs one by one.

*Petal margin*.—Typically entire. A few of the innermost petal margins are emarginate.

*Petal shape*.—Obovate. Apex: Typically apiculate, occasionally retuse on some innermost petals. Base: Cuneate.

*Petal size*.—19 to 30 mm (l)×7 to 35 mm (w).

*Petal arrangement*.—Formal.

*Texture*.—Inner Side: Leathery. Outer Side: Leathery.

Petaloids:

*Petaloid count*.—Average of 10 per flower.

*Petaloid size*.—7 to 16 mm (l)×3 to 15 mm (w).

*Petaloid color*.—Inner side: Red 44B. Outer side: 45C. Intonations of White Group 155A present on midrib of both sides.

*Petaloid texture*.—Inner Side: Smooth. Outer Side: Smooth.

*Margins*.—Undulated.

*Petaloid shape*.—Obovate to Obcordate, with many petaloids highly irregular. Apex: Emarginate. Base: Attenuate.

Reproductive organs:

*Pistils*.—Approximately 50 present. Stigmas: Location: Slightly superior in position to anthers. Color: Yellow-White Group 158A. Styles: Length: About 5 to 10 mm long. Color: Red Group 45A, with intonations of Yellow-White Group 158A.

*Stamens*.—Approximately 40 on average and regularly arranged. Anthers: Size: Average 2 to 3 mm (l)×1 to 2 mm (w). Color: Yellow-White Group 158A with intonations of Red Group 54A. Pollen: Generally present. Color: Greyed-Yellow 161B. Filaments: Color: Yellow Group 4B with intonations of Red Group 54B. Length: 4 to 6 mm.

*Receptacle*.—Surface: Abundant stipitate glands and small prickles present. Color: Yellow-Green Group 144A to 144B. Intonations of Greyed-Purple Group 183C present on stipitate glands. Shape: Urn-shaped. Texture: Hispid. Size: 5 to 7 mm (h)×10 to 12 mm (w).

*Peduncle*.—Surface: Abundant stipitate glands and small prickles present. Length: 45 to 65 mm average length. Diameter: 2 to 4 mm average diameter. Color: Yellow-Green Group 146A to 146B, with intonations of Greyed-Purple 183C present on stipitate glands. Strength: Somewhat strong. Texture: Hispid. Borne: Singularly. Flowers held upright.

THE PLANT

Growth: Moderately vigorous.

Plant habit: Compact. Upright to bushy. When grown as a 15 cm pot plant, the average plant height is 30 to 35 cm and the average plant width is 20 to 25 cm.

Stems:

*Stem color*.—Young wood: Yellow-Green Group 144C. Older wood: Yellow-Green Group 146A.

*Stem surface texture*.—Young wood: Smooth. Older wood: Smooth.

*Length*.—20 to 25 mm average length when grown under commercial greenhouse floral production.

*Diameter*.—3 to 5 mm average diameter.

Prickles: Present.

*Incidence*.—Average of 13 per each 10 cm of stem.

*Size*.—Average length: 3 to 5 mm.

*Color*.—Immature prickles: Yellow-Green Group 145C. Mature prickles: Yellow-Green Group 145C. Intonations: Greyed-Red Group 181C and 181D.

*Shape*.—Deeply concave.

Leaves: Normally 5 leaflets on normal leaves in middle of the stem.

*Venation pattern*.—Pyramidal net pattern.

*Leaf size*.—80 to 100 mm (l)×55 to 75 mm (w).

*Abundance*.—Abundant.

Leaflets:

*Size*.—Average size of the terminal leaflet is 35 to 45 mm (l)×20 to 25 mm (w).

*Shape*.—Elliptic to acuminate. Base: Obtuse. Apex: Acute to acuminate.

*Margins*.—Serrated.

*Surface*.—Semi-glossy.

*Texture*.—Upper side of leaflet: Smooth. Under side of leaflet: Leathery.

*Color, mature foliage*.—Upper Leaflet Surface: Green Group 139A. Lower Leaflet Surface: Yellow-Green Group 146B.

*Color, juvenile foliage*.—Upper Leaflet Surface: Yellow-Green Group 146A. Lower Leaflet Surface: Yellow-Green Group 146B.

*Anthocyanin intonation*.—Greyed-Purple 183C. Location: Present on leaflet margins.

*Arrangement*.—Odd pinnate.

*Venation*.—Reticulate.

Stipules:

*Size*.—15 to 18 mm (l)×6 to 8 mm (w).

*Stipule color*.—Yellow-Green Group 146A, Yellow-Green Group 146D on midrib.

*Anthocyanin*.—Greyed-Purple 183C present on margins.

*Stipitate glands*.—Abundant numbers present on margins.

*Margins*.—Glandular toothed.

*Texture*.—Glabrous.

*Shape*.—Apex: Apiculate. Base: Winged.

Petiole:

*Length*.—Average 25 mm.

*Diameter*.—Average 1 mm.

*Petiole color*.—Upper surface: Yellow-Green Group 146A. Underneath: Yellow-Green 146B.

*Margins*.—Glandular toothed, with limited numbers of stipitate glands.

*Anthocyanin*.—Greyed-Red Group 183C, present on margins and upper surface.

*Prickles*.—Occasionally one small prickle underneath.

*Stipitate glands*.—Limited numbers present on margins only.

*Texture*.—Upper surface: Papillate and pubescent. Underneath: Glabrous.

Petiole rachis:

*Length*.—Average 10 to 15 mm.

*Diameter*.—Average 1 mm.

*Color*.—Yellow-Green Group 146A.

*Anthocyanin*.—Greyed-Red Group 183C present on margins and upper surface.

*Margins*.—Entire with occasional stipiate glands present.

*Prickles*.—A few small prickles underneath.

*Stipitate glands*.—Limited numbers of stipitate glands on margins.

Hips/seed formation: None observed.

Winter hardiness: Due to its primary use in greenhouse culture, winter hardiness of the variety has not been evaluated.

Disease resistance: Above average resistance to Powdery mildew (*Sphaerotheca pannosa* and *Botrytis* (*Botrytis cinerea*) diseases under normal growing conditions in Jackson County, Oreg.

I claim:

1. A new and distinct variety of rose plant, as described and illustrated herein.

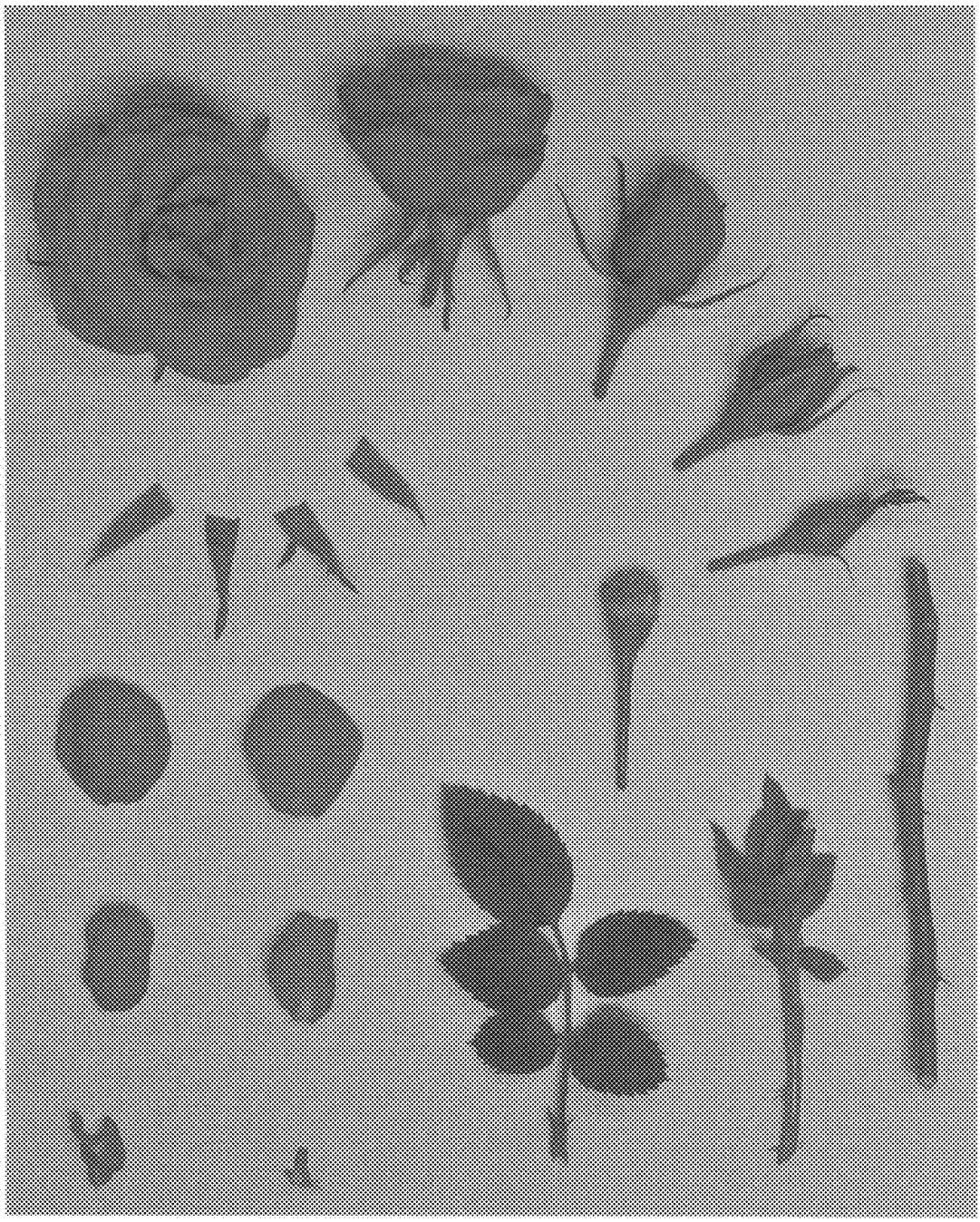

* * * * *